United States Patent [19]

Kleyer et al.

[11] Patent Number: 5,068,387

[45] Date of Patent: Nov. 26, 1991

[54] PRODUCTION OF ORGANOFUNCTIONAL ALKOXYSILANES

[75] Inventors: Don L. Kleyer, Hemlock; John L. Speier, Midland, both of Mich.

[73] Assignee: Dow Corning Corporation, Midland, Mich.

[21] Appl. No.: 444,345

[22] Filed: Dec. 1, 1989

[51] Int. Cl.$^5$ .......................... C07F 7/08; C07F 7/10; C07F 7/18

[52] U.S. Cl. ..................... 556/485; 556/410; 556/413; 556/412; 556/445; 556/478; 556/482

[58] Field of Search ............... 556/410, 413, 445, 412, 556/478, 482, 485

[56] References Cited

U.S. PATENT DOCUMENTS

| | | | |
|---|---|---|---|
| 2,521,267 | 9/1950 | Tiganik | 260/448.8 |
| 2,985,678 | 5/1961 | Chappelow | 260/448.8 |
| 4,683,321 | 7/1987 | Nelson | 556/478 |
| 4,888,436 | 12/1989 | Shiozawa et al. | 556/413 |
| 4,897,501 | 1/1990 | Takatsuna et al. | 556/413 |
| 4,921,988 | 5/1990 | Takatsuna et al. | 556/413 |

FOREIGN PATENT DOCUMENTS

| | | | |
|---|---|---|---|
| 598444 | 5/1960 | Canada | 556/478 |
| 573906 | 12/1945 | United Kingdom | 556/478 |
| 668532 | 3/1952 | United Kingdom | 556/478 |

OTHER PUBLICATIONS

Ryan, John W., J. Amer. Chem. Soc., 84:4730–34, 1962.

Primary Examiner—Paul F. Shaver
Attorney, Agent, or Firm—William F. Boley

[57] ABSTRACT

The present invention relates to a process for the production of mixtures of novel organofunctional alkoxysilanes by the reaction of mixtures of certain substituted organic halides and chlorosilanes with molten sodium dispersed in alkoxysilanes. In the described process, the substituted organic groups of the organic halide replace alkoxy groups of the alkoxysilanes. Also claimed, are organofunctional alkoxysilanes prepared by the claimed process.

7 Claims, No Drawings

PRODUCTION OF ORGANOFUNCTIONAL ALKOXYSILANES

BACKGROUND OF THE INVENTION

This invention relates to a process for the production of mixtures of novel organofunctional alkoxysilanes by the reaction of mixtures of certain substituted organic halides and chlorosilanes with molten sodium dispersed in alkoxysilanes. In the described process, the substituted organic groups of the organic halide replace alkoxy groups of the alkoxysilanes.

The literature contains many examples of the reaction of sodium with chlorosilanes. For example, it is commonly known that sodium reacts with chlorosilanes to form polysilanes and sodium chloride. Sodium also reacts with organic halides by the well known Wurtz reaction which can be written in equation form as:

$$2RX + 2Na \rightarrow 2NaX + RR \qquad (1)$$

Our work has shown that molten sodium may be dispersed in alkoxysilanes at about 100° C. and little reaction can be observed in many hours. Ryan, J. W., J. Amer. Chem. Soc. 84:4730-34, 1962, demonstrated that at more elevated temperatures, reduction of alkoxysilanes occurred to form alkylsilanes.

When molten sodium was dispersed in refluxing tetramethoxysilane at 122° C., 24 percent of the tetramethoxysilane was converted to methyltrimethoxysilane in 84 hours. Ryan, supra, proposed that this conversion proceeded through the following two step process:

$$(MeO)_4Si + 2Na \rightarrow (MeO)_3SiONa + Na\text{---}CH_3 \qquad (2)$$

$$(MeO)_4Si + Na\text{---}CH_3 \rightarrow MeSi(OMe)_3 + NaOMe \qquad (3)$$

Our work has shown that molten sodium dispersed in PhSi(OMe)$_3$ at 125° C. for 72 hours formed nine percent phenylmethyldimethoxysilane in a similar manner.

British Patent 573,906, issued Dec. 12, 1945, to Revertex, Ltd., teaches that the dropwise addition of iso-amyl bromide to a dispersion of molten sodium in a solution of tetramethoxysilane formed iso-amyl-Si(OMe)$_3$ and (iso-amyl)$_2$Si(OMe)$_2$. Other examples taught that the same procedure formed substituted ethoxysilanes when chlorobenzene, cyclohexylbromide, benzyl chloride, ethyl bromide, or n-octyl bromide was added to a dispersion of molten sodium in tetraethoxysilane.

Tiganik, L., U.S. Pat. No. 2,521,267, issued Sept. 5, 1950, claimed a method of reducing the consistency of the mixture of products obtained by bubbling a gaseous mixture of tetrachlorosilane and methylchloride into a stirred dispersion of molten sodium in tetraethoxysilane activated by a small amount of copper, tin, or silver. In this process, all of the methyl chloride was absorbed. Distillation after filteration gave about an 85% yield of principally MeSi(OEt)$_3$ with some Me$_2$Si(OEt)$_2$ and a very small quantity of Me$_3$SiOEt. This patent claimed the method in which an alkyl chloride is added as a mixture with an acid substance, such as tetrachlorosilane, in order to quickly neutralize the sodium alkoxide formed during the reaction making the reaction product more easily filterable.

Tiganik, L., British Patent 668,532, issued Mar. 18, 1952, claims a method for reducing the consistency of products formed when ethyl bromide is added to a dispersion of molten sodium in tetraethoxysilane. High consistency makes stirring the reacting dispersion of molten sodium very difficult and makes filtration of the end mixture nearly impossible. The patent teaches that the high consistency of the mixture is due to the presence of NaOEt and that filtration is facilitated by acidifying the final mixture with SiCl$_4$, HCl, acetic anhydride or any other acidic substance.

Tiganik, L., Canadian Patent 598,444, issued May 24, 1960, teaches a process in which 400 moles of chlorobenzene mixed with 100 moles of tetrachlorosilane was added to molten sodium dispersed in tetraethoxysilane. Decomposition of the sodium alkoxide compound formed in the reaction is effected by carrying out the reaction in the presence of tetrachlorosilane.

Chappelow, C., et al., U.S. Pat. No. 2,986,687, issued May 23, 1961, claims a process whereby a tertiary lower alkyl halide mixed with a chlorosilane is added to an alkoxysilane in the presence of sodium, at 115° C. and with vigorous stirring, to make tertiary alkylalkoxysilanes. The alkoxysilanes employed as reactants were of the general formula R$_a$Si(OR')$_4$$_a$; where R and R' were selected from a group consisting of alkyl, aryl, substituted alkyl, and substituted aryl radicals. When R or R' was a substituted alkyyl or aryl hydrocarbon radical the substituent was selected from the group consisting of alkoxy, aryloxy, alkyl-thio, arylthio, dialkylamino and trialkylsilyl groups.

The instant invention is a process using certain substituted organohalides to make a variety of organofunctional alkoxysilanes. The instant invention also includes a variety of novel organofunctional alkoxysilanes capable of being prepared by the described process. The claimed organofunctional alkoxysilanes are useful in forming copolymers and as coupling agents.

DESCRIPTION OF THE INVENTION

The present invention relates to a process for the production of novel organofunctional alkoxysilanes by the addition of a mixture consisting of a substituted organic halide and a chlorosilane to a dispersion of molten sodium in an alkoxysilane. Also claimed, are novel organofunctional alkoxysilanes compositions prepared by the described process.

More specifically, the present invention is a process for preparing organofunctional alkoxysilanes of the formula $$R^1_aR^2_b(AR)_nSi(OR^3)_{4-a-b-n};$$

where $R^1$ and $R^2$ are independently selected from the group consisting of alkyl, aryl, and AR radicals; $R^3$ is an alkyl of 1 to 7 carbon atoms; A is a substituent on an organic group, R, said A selected from the group consisting of $R^4O-$, $C_zF_{2z+1}-$, $R^4R^5N-$, and alkenyl radicals; R4 and R5 are independently selected from the group consisting of alkyl, aryl, and triorganosilyl radicals; z is 1 to 4; R is a divalent radical of the structure $-R^6(CH_2)_m-$, $R^6$ is selected from a group consisting of primary aliphatic and aromatic divalent radicals; m=0 to 6; n=1, 2, or 3; a+b+n=1, 2, or 3; and a+b=0, 1, or 2.

The process of the present invention comprises:

(A) forming a mixture of an organic halide of formula $$(AR)X;$$

where AR is a substituted organic radical as previously described and X is selected from the group consisting of chloride, bromide, and iodide; with about an equivalent of a chlorosilane;

(B) forming a dispersion of molten sodium in an alkoxysilane of formula $$R^1_a R^2_b Si(OR^3)_{4-a-b};$$

where $R^1$, $R^2$, and $R^3$ are as previously described, and $a+b=0$, 1, or 2;

(C) adding the mixture of step (A) to the dispersion of step (B) to form a second mixture at a temperature of 100° to 200° C. in which the organofunctional alkoxysilane is formed.

The organofunctional alkoxysilanes can be, for example, allylmethyldimethoxysilane, (styrylmethyl)methyldimethoxysilane, (styrylmethyl)trimethoxysilane; bis(3,3,3-trifluoropropyl)dimethoxysilane; bis(ethoxymethyl)-diethoxysilane; ((4-N,N-dimethylamino)-phenyl)methyldimethoxysilane; and (4-N,N-bis(trimethylsilyl)aminophenyl)-trimethoxysilane.

The organohalide, (AR)X, is composed of a substituted organic radical (AR) and a halide. The halide constitutent can be chloride, bromide, or iodide atoms. Preferred are chloride atoms.

The substituent A of the organohalide can be, for example, an alkenyl, alkenylaryl, di-substituted amino, alkoxide, phenoxide, or fluorinated hydrocarbon radical. The alkenyl radical can be, for example, a vinyl or alkylvinyl radical. The alkenylaryl radical can be, for example, vinylphenyl or 1-methylethenylphenyl. The substituent A can be fluorinated hydrocarbons radicals, for example, trifluoromethyl or perfluorobutyl.

The substituent A of the organohalide can form an ether linkage with $R^6$ of the divalent radical to form ether radicals of the general formula $R^4OR^6(CH_2)_m$—, where $R^4$ is an alkyl, aryl, or triorganosilyl radical. Preferred, are ether radicals where $R^6$ is —$CH_2$-and $m=0$ or 2, and $R^4$ is methyl, ethyl, or phenyl. Examples of alkyl ethers useful for the present invention are chloromethyl ethyl ether and bromomethyl propyl ether.

The substituent A of the organohalide can be a di-substituted amino radical of the formula $R^4R^5N$—, where $R^4$ and $R^5$ are independently selected alkyl groups of 1 to 18 carbon atoms, aryl, or triorganosilyl groups. The preferred triorganosilyl radical is trimethylsilyl. Examples of substituted aryl organohalides are: 4-bromo-N,N-dimethylaniline and N,N-bis(trimethylsilyl)-4-chloroaniline.

The substituent R of the organohalide is a divalent group which links the functional substituent A to the halide atom X. Similarily, after the reaction, R serves to link the functional substituent A to the silicon atom in the organofunctional alkoxysilane. The substituent R may be further defined by the formula —$R^6(CH_2)_m$—, where m is an integer from 0 to 6 and $R^6$ is selected from a group consisting of primary aliphatic and aromatic divalent radicals. For example, $R^6$ can be a primary aliphatic divalent radical such as methylene, dimethylene, tetramethylene, or 2-methyltetramethylene; or an aromatic divalent radical such as phenylene, —$CH_2$·Ph—, or —$(CH_2)_2Ph$—, where Ph is a phenyl radical.

A preferred, but not limiting embodiment of the described process, is when a mixture of about equivalent amounts of a substituted organic halide and a chlorosilane is added to about two equivalents of molten sodium dispersed in an alkoxysilane, and reacted in about the following proportions:

$$R^1_a R^2_b Si(OR^3)_{4-a-b} + 2yNa + y(AR)X + \quad (4)$$
$$\frac{y}{4-a-b} R^1_a R^2_b SiCl_{4-a-b} \longrightarrow$$
$$R^1_a R^2_b(AR)_n Si(OR^3)_{4-a-b-n} + yNaX + yNaCl;$$

where $R^1$, $R^2$, $R^3$, AR, X, a, and b are as previously described; $n=1$, 2, or 3; and y is the mole ratio of (AR)X to:

$$R^1_a R^2_b Si(OR^3)_{4-a-b} + \frac{y}{4-a-b} R^1_a R^2_b SiCl_{4-a-b}.$$

It is preferred, that the mole ratio y be between about 0.3 and three. Under the conditions described in equation 4, there is a near quantitative conversion of the chlorosilane to alkoxysilane. This simplifies the separation of the resultant product. The resultant product is a mixture of organofunctional alkoxysilanes with the average number of organofunctional substitutions on the silicon atom, n, being a function of y.

The described reactions can be ran at a temperature of about 100°-200° C. A preferred temperature range is about 100°-120° C.

The organic halide is mixed with the chlorosilane. It is preferred, that the organic halide and chlorosilane be mixed in about equivalent amounts or with a slight excess of chlorosilane. The term about equivalent amounts is meant to encompass slight variations from equivalence that do not significantly alter the course of the reaction. By equivalent amount is meant, the number of chlorine atoms present as chlorosilane is equal to the number of moles of organic halide. By slight excess of chlorosilane is meant, less than a 10 mole percent excess of chloride in relation to the moles of organic halide present.

Any chlorosilane can be used, but many result in the formation of complex mixtures of alkoxysilane products which may be difficult to separate. The preferred chlorosilane is of the formula $R^1_a R^2_b SiCl_{4-a-b}$; where $R^1$ and $R^2$ are as previously described and $a+b=0$, 1, or 2. The preferred chlorosilane is shown in equation (4), above. Inherent in equation 4 is the understanding that $R^1$ and $R^2$ are the same in the cholorsilane and the alkoxysilane.

Trimethylchlorosilane can be a preferred chlorosilane leading to no separation problems. With trimethylchlorosilane, equation (4) becomes:

$$R^1_a R^2_b Si(OR^3)_{4-a-b} + 2yNa + y(AR)X + yMe_3SiCl \longrightarrow \quad (5)$$
$$R^1_a R^2_b(AR)_n Si(OR^3)_{4-a-b-n} + yNaX + yNaCl + yMe_3SiOR^3.$$

In this case, y is the mole ratio of (AR)X to the alkoxysilane.

Examples of other chlorosilanes that may be useful are: tetrachlorosilane, methyltrichlorosilane, ethyltrichlorosilane, ethyldichlorosilane, 3,3,3-trifluoropropyltrichlorosilane, vinylbenzyltrichlorosilane, and methoxymethyltrichlorosilane.

The molten sodium is dispersed in an alkoxysilane or in a solution containing an alkoxysilane. The dispersion can be formed by first melting the sodium and then adding it to the alkoxysilane with sufficient agitation of the mixture to effect a dispersion. Alternatively, solid sodium can be added to the alkoxysilane, heated until it melts, and then dispersed by agitation. Preferred is a ratio of two moles of sodium per mole of organic halide. Lesser amounts of sodium can be used but will lead to incomplete reaction. Little advantage is gained in increasing the mole ratio of sodium to organic halide much above two. In practice, the reaction may be run with a slight excess of sodium to insure completion of the reaction. By slight excess is meant a ratio of sodium to organic halide greater than 2:1 but less than 2.1:1.

If instead of (AR)X being a primary or an aryl halide, a substituted secondary or tertiary halide, such as ACMeHX or ACMe$_2$X is employed in the reaction, dehydrohalogenation occurs as a competitive reaction with sodium to form ACH=CH$_2$ or ACMe=CH$_2$ to reduce the yield of organofunctional alkoxysilanes. If the structure of A contains a carbonyl group, as in an aldehyde, ketone, or carboxylate ester, the intermediate ARNa reacts with that group as fast or faster than with an alkoxysilane to form polymers instead of the desired substituted alkoxysilanes. If A contains an active hydrogen atom, such as found in —OH or —NH structures, the intermediate ARNa reacts to form ARH and O—Na or N—Na products instead of the desired substituted alkoxysilanes.

The alkoxysilane can be, for example, tetramethoxysilane, tetraethoxysilane, dimethyldihexoxysilane, methyltrimethoxysilane, 3,3,3-trifluoropropyltrimethoxysilane, diphenyldimethoxysilane, vinylmethyldimethoxysilane, and vinylbenzylmethyldimethoxysilane.

The mixture comprising an organic halide and chlorosilanes is added to the dispersion of molten sodium in alkoxysilanes. Under the preferred conditions, described supra, the number of moles of chloride present as chlorosilane is equal to or in slight excess of the moles of organic halide. Under these conditions, the reaction medium remains neutral or acidic at all times. This reduces the viscous consistency of the mixtures produced by the reaction and stirring of the dispersion is facilitated. The formation of sodium alkoxides is suppressed.

The described reactions are highly exothermic and very rapid. An inert, volatile, diluent may be added to the mixture. Reflux of the diluent removes heat from the mixture and permits the process to be completed rapidly without danger of overheating the reaction mixture. However, the reflux temperature of the solutions must remain above about 99° C. so that the sodium remains liquid. The inert diluent may be an organic solvent, for example, isooctane, heptane, or toluene.

Isolation and recovery of the organofunctional alkoxysilanes can be effected by standard methods, for example, filtration and distillation of the filtrate.

So that those skilled in the art may better understand and appreciate the instant invention the following examples are presented. These examples are presented to be illustrative and are not to be construed as limiting the claims delineated herein.

EXAMPLE 1

(Not within the scope of the present invention) Sodium (202.5 g, 8.81 mol) was dispersed by vigorous stirring in tetraethoxysilane (305.8 g, 1.47 m) and heptane (458 ml) at reflux (102° C.). A solution of tetrachlorosilane (187.7 g, 1.11 moles, 4.44 equiv. of chloride) in chlorobenzene (496 g, 4.41 mole) was added at a rate to maintain the mixture at gentle reflux with no external heating. The addition was completed and refluxing ceased in 77 minutes.

The slurry which was formed during the reaction was vacuum filtered and the filtrate was analyzed by gas liquid chromatography (GLC). The solids in the filter were washed with dichloromethane, dried and weighed. The solids weighed 524 g which is close to the expected calculated weight of 515.4 for 8.81 moles of sodium chloride.

GLC analysis of the recovered filtrate could detect no biphenyl and no ethylsilanes. The GLC analysis indicated the filtrate contained heptane, tetraethoxysilane (56 g), phenyl-triethoxysilane (134 g), diphenyldiethoxysilane (314 g), tri-phenylethoxysilane (119 g), tetraphenylsilane (9 g). These products contained 95% of the phenyl groups added as chlorobenzene.

EXAMPLE 2

(Not within the Scope of the present invention) A series of reactions was ran similar to that of Example 1 to illustrate the impact of the proportions of the reactants on the process. The reactions were run according to the following equation:

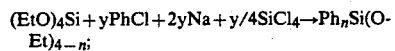

$$(EtO)_4Si + yPhCl + 2yNa + y/4 SiCl_4 \rightarrow Ph_nSi(OEt)_{4-n};$$

where y = mole PhCl/(moles $(EtO)_4Si + y/4$ SiCl$_4$).

The results are presented in Table 1.

TABLE 1

| | Mole % Phenylsilanes | | | |
|---|---|---|---|---|
| y | n = 1 PhSi(OEt)3 | n = 2 Ph2Si(OEt)2 | n = 3 Ph3SiOEt | n = 4 Ph4Si |
| 1.33 | 38 | 50 | 11 | ~1 |
| 1.71 | 24 | 57 | 18 | ~1 |
| 2.0 | 13 | 57 | 29 | ~1 |

As evident from the data presented in Table 1, the distribution of organic alkoxysilanes is very much a function of y.

EXAMPLE 3

(Not within the scope of the present invention) Sodium (2.82 g, 0.0123 mol) was dispersed in dimethyldi-n-hexoxysilane (34.3 g, 0.13 mol) at 104° C. Dropwise addition of a mixture of chlorobenzene (6.9 g, 0.06 mol) and dimethyldichlorosilane (4 g, 0.03 mol) caused the temperature of the dispersion to rise to 170° C. in one minute. External cooling with a cold water bath and a reduced rate of addition lowered the temperature to 130° C. where it was maintained until the addition was completed in a total time of seven minutes.

Analysis by gas chromotography using a mass spectrometer detector GC/MSD indicated a quantitative yield of dimethylphenyl-n-hexoxysilane. No phenyl chloride, dimethyl-diphenylsilane, biphenyl, or chlorosilanes were detected.

EXAMPLE 4

Sodium (209 g, 9.1 mol) was dispersed in methyltrimethoxysilane (2783 g, 20.5 mol) at reflux, 102° C. Allyl chloride (400 g, 5.2 mol) mixed with methyltrichlorosilane (226 g, 1.52 mol, 4.6 equiv Cl) was added dropwise to the dispersion.

After the addition was completed, the mixture was filtered and the filtrate was distilled. Upon distillation, a small amount of excess allyl chloride was obtained followed by MeSi(OMe)$_3$, MeAllylSi(OMe)$_2$ (366 g, 2.5 mol), and Me(Allyl)$_2$SiOMe (66 g, 0.42 mol). The remaining undistilled residue was analyzed by GLC as containing Me(Allyl)$_2$SiOMe and Me(Allyl)$_3$Si and small amounts of several unidentified high boiling materials.

EXAMPLE 5

Sodium (3.10 g, 0.135 mol) was dispersed in methyltrimethoxysilane (33 ml, 0.23 mol) at reflux. A mixture of the meta and para isomers of chloromethylstyrene (10.3 g, 0.068 mol) and methyltrichlorosilane (3.38 g, 0.023 mol) was added dropwise over a nine minute period. The resultant mixture was analyzed by GLC/MSD. The mixture consisted of, in area percentages: 80.7 methyltrimethoxysilane, 1.8% chloromethylstyrene, 13.2% (styrylmethyl)methyldimethoxysilane, 1% 1,2 bis-(4-vinylphenyl)ethane, and about 4% of unidentified impurities.

EXAMPLE 6

Sodium (3.7 g, 0.16 mol) was dispersed in methyltrimethoxsilane (47 g, 0.35 mol) at reflux. A mixture of 1-bromo, 3,3,3-trifluoropropane (14.2 g, 0.08 mol), and methyltrichlorosilane (4.0 g, 0.027 mol) was added dropwise. After the addition was complete, the mixture was filtered and the filtrate was analyzed by GLC. The mixture consisted of, in area percentages: 1.3% 1-bromo,3,3,3-trifluoropropane, 84.5% methyltrimethoxysilane, 10.9% methyl-(3,3,3-trifluoropropyl)dimethoxysilane, and 1.2% bis-(3,3,3-trifluoropropyl)methylmethoxysilane.

EXAMPLE 7

Sodium (15.2 g, 0.66 mol) was dispersed in tetramethoxysilane (16.82 g, 0.11 mol) and toluene (125 ml) at 103° C. A mixture of 1-bromo,3,3,3-trifluoropropane (58.5 g, 0.33 mol) and tetrachlorosilane (14.2 g, 0.083 mol) was added dropwise in 24 minutes. During this addition, 115 ml of toluene was also added. The mixture was filtered at 50° C. thru a coarse sintered glass filter. The solids were washed twice with 100 ml portions of toluene and all liquids were combined and analyzed by GLC/MS. In area percent, the products were: 50% 3,3,3-trifluoropropyltrimethoxysilane, 30% bis-(3,3,3-trifluoropropyl)dimethoxysilane, 20% tris-(3,3,3-trifluoropropyl)methoxysilane, and less than 1% tetrakis-(3,3,3-trifluoropropyl)silane. No unreacted bromide or chlorosilanes were detected.

EXAMPLE 8

Sodium (80.4 g, 3.5 mol) was dispersed in 3,3,3-trifluoropropyltrimethoxysilane (130 g, 0.6 mol) and 2860 ml isooctane. A mixture consisting of 1-bromo, 3,3,3-trifluoropropane (265 g, 1.5 mol) and 3,3,3-trifluoropropyltrichlorosilane (116 g, 0.5 mol) was added dropwise over 99 minutes. No external heat was applied. Upon completion of the addition, the resultant slurry was cooled to 40° C. and easily filtered through a coarse sintered glass funnel using vacuum. The filtrate was analyzed by GC as containing the following area percentages of products: 68% bis-(3,3,3-trifluoropropyl)-dimethoxysilane, 28% tris-(3,3,3-trifluoropropyl)methoxysilane, and 4% 3,3,3-trifluoropropyltrimethoxysilane. Peak identities were confirmed by GC/MS analysis.

EXAMPLE 9

Sodium (1.88 g, 0.082 mol) was dispersed in 3,3,3-trifluoropropyltrimethoxysilane (16.54 g, 0.076 mol) and 25 ml of isooctane at reflux (107° C.) and a mixture of 1-bromo,3,3,3-trifluoropropane (7.26 g, 0.041 mol) and trimethylchlorosilane (4.42 g, 0.041 mol) was added dropwise. When about half of the mixture was added, the reflux temperature of the mixture fell below 99° C. because of the formation of Me$_3$SiOMe (b.p. 56° C.); the sodium solidified and the reaction slowed. Toluene (25 ml) was added to elevate the reflux temperature and the addition was completed. The process took about 2 hours. GC analyses with peak identification by GC/MS gave the following area percentages of products: 25% trimethylmethoxysilane, 45.3% 3,3,3-trifluoropropyltrimethoxysilane, 21% bis-(3,3,3-trifluoropropyl)dimethoxysilane, and 5.5% tris-(3,3,3-trifluoropropyl)methoxysilane.

EXAMPLE 10

Sodium (1.99 g, 0.86 mol) was dispersed in tetraethoxysilane (37.2 g, 0.18 mol) at 108° C. and a mixture of chloromethyl ethyl ether (4.2 g, 0.044 mol) and tetrachlorosilane (1.86 g, 0.011 mol) was added dropwise at a rate to maintain the dispersion at about 120° C. with no external heating. As soon as the addition was complete GLC analysis indicated the following compounds in area percent: 90.5% tetraethoxysilane; 4.0% (ethoxymethyl)triethoxysilane, (EtO)$_3$SiCH$_2$OEt; 0.53% di(ethoxymethyl)diethoxysilane, (EtO)$_2$Si(CH$_2$OEt)$_2$; 35% tri(ethoxymethyl)ethoxysilane, EtOSi(CH$_2$OEt)$_3$; and 2.8% tetraethoxymethylsilane, Si(CH$_2$OEt)$_4$.

EXAMPLE 11

Sodium (2.22 g, 0.096 mol) was dispersed in refluxing methyltrimethoxysilane (20 ml, 0.14 mol) and a mixture of 4-bromo-N,N-dimethylaniline (9.67 g, 0.048 mol) and methyltrichlorosilane (2.41 g, 0.016 mol) dissolved in methyltrimethoxysilane (10 ml, 0.07 mol) was added dropwise in one minute. The liquid was then analyzed by GC/MS as consisting in area percentages of 0.6% unreacted 4-bromo-N,N-dimethylaniline; 74% methyltrimethoxysilane and 24.7% ((4-N,N-dimethylamino)-phenyl) methyldimethoxysilane.

EXAMPLE 12

Sodium (2.42 g, 0.1 mol) was dispersed in tetramethoxysilane (49 g, 0.32 mol) at 112° C. and a mixture of N,N-bis(trimethylsilyl)-4-chloroaniline (13 g, 0.048 mol) and tetrachlorosilane (2.06 g, 0.012 mol) was added dropwise over 34 minutes to maintain the dispersion at 110°–115° C. with no external heating. Immediately after the addition was completed, the liquid was analyzed by GC. The area percentages of components of the liquid were: 78% tetramethoxysilane, 18.1% N,N-bis(trimethylsilyl)-4-(trimethoxysilyl) aniline. The identity of the product was confirmed by GC/MS analysis.

What is claimed is:

1. An organofunctional alkoxysilane of formula

where $R^1$ and $R^2$ are independently selected from the group consisting of alkyl, aryl, and AR radicals; $R^3$ is an alkyl of 1 to 7 carbon atoms; A is a substituent on an organic group, R, said A selected from the group consisting of $R^4O-$, $C_zF_{2z+1}-$, and alkenyl radicals; $R^4$ and $R^5$ are independently selected from the group consisting of alkyl, aryl, and triorganosilyl radicals; z is 1 to 4; R is a divalent radical of the structure $-R^6(CH_2)_m-$, $R^6$ is selected from a group consisting of aliphatic and aromatic divalent radicals; m=0 to 6; n=2 or 3; a+b+n=2 or 3; and a+b=0 or 1.

2. The organofunctional alkoxysilane of claim 1, where $R^3$ is selected from the group consisting of methyl and ethyl radicals.

3. The organofunctional alkoxysilane of claim 2, where $R^6$ is selected from the group consisting of $-CH_2-$, $-CH_2CH_2-$, and phenyl bi-radical, and m=0.

4. The organofunctional alkoxysilane of claim 3 where substituent A is selected from the group consisting of vinyl, vinylphenyl, and 1-methylethenylphenyl radicals.

5. The organofunctional alkoxysilane of claim 3, where substituent A is the $R^4O-$ radical.

6. The organofunctional alkoxysilane of claim 3, where substituent A is the $C_zF_{2z+1}-$ radical.

7. The organofunctional alkoxysilane of claim 3, where the $C_zF_{2z+1}-$ radical is trifluoromethyl.

* * * * *